(12) United States Patent
Cazeneuve et al.

(10) Patent No.: US 12,121,680 B2
(45) Date of Patent: Oct. 22, 2024

(54) MEDICAL DEVICE COMPRISING A SMART HANDLE FOR IMPROVING HANDLING OF AN ELONGATED FUNCTIONAL SYSTEM

(71) Applicant: BASECAMP VASCULAR, Paris (FR)

(72) Inventors: Jean-Baptiste Cazeneuve, Ivry-sur-seine (FR); Camille Maiano, Brélès (FR)

(73) Assignee: BASECAMP VASCULAR, Paris (FR)

( * ) Notice: Subject to any disclaimer, the term of this patent is extended or adjusted under 35 U.S.C. 154(b) by 988 days.

(21) Appl. No.: 16/973,222

(22) PCT Filed: Jun. 20, 2019

(86) PCT No.: PCT/EP2019/066372
§ 371 (c)(1),
(2) Date: Dec. 8, 2020

(87) PCT Pub. No.: WO2019/243515
PCT Pub. Date: Dec. 26, 2019

(65) Prior Publication Data
US 2021/0252257 A1    Aug. 19, 2021

(30) Foreign Application Priority Data

Jun. 20, 2018  (EP) .................................... 18305778

(51) Int. Cl.
*A61M 25/09*    (2006.01)
*A61B 1/005*    (2006.01)
(Continued)

(52) U.S. Cl.
CPC ........ *A61M 25/09* (2013.01); *A61M 25/0136* (2013.01); *A61M 25/0158* (2013.01);
(Continued)

(58) Field of Classification Search
CPC .............. A61M 25/09; A61M 25/0136; A61M 25/0158; A61M 2025/09116;
(Continued)

(56) References Cited

U.S. PATENT DOCUMENTS 5,025,799 A    6/1991  Wilson
5,137,288 A    8/1992  Starkey et al.
(Continued)

FOREIGN PATENT DOCUMENTS

EP    0 543 539 A1    5/1993
EP    3 326 549 A1    5/2018

OTHER PUBLICATIONS

International Search Report and Written Opinion of the International Searching Authority issued on Sep. 11, 2019 in corresponding International application No. PCT/EP2019/066372; 12 pages.

*Primary Examiner* — Alex M Valvis
*Assistant Examiner* — Justin Xu
(74) *Attorney, Agent, or Firm* — Maier & Maier, PLLC

(57) ABSTRACT

For surgical and/or medical instruments, a smart handle for easily and more accurately manipulating an elongated functional system inside the body of a subject, including a handle body extending along a longitudinal axis having a first electrical interface including at least two electrical connectors, a second electrical interface with at least two circular conductive elements and a chamber for receiving a power supply; the power supply being connected to one of the electrical interfaces, at least one first external command being arranged on the outer surface of the handle body, and when activated, the first external command allows to flow an electrical current through the electrical connectors; the electrical connectors being maintained in contact with the other electrical interface by a spring force, the electrical connectors including at their distal end a round tip for ensuring a
(Continued)

permanent contact between the electrical connectors and the circular conductive elements during rotation.

13 Claims, 4 Drawing Sheets

(51) Int. Cl.
    *A61B 1/01*     (2006.01)
    *A61B 17/00*     (2006.01)
    *A61B 17/29*     (2006.01)
    *A61B 34/30*     (2016.01)
    *A61M 25/01*     (2006.01)

(52) U.S. Cl.
    CPC ... *A61B 1/0052* (2013.01); *A61B 2017/00318* (2013.01); *A61B 2017/00867* (2013.01); *A61M 2025/09116* (2013.01); *A61M 2205/0266* (2013.01); *A61M 2205/586* (2013.01); *A61M 2205/8206* (2013.01)

(58) Field of Classification Search
    CPC .... A61M 2205/0266; A61M 2205/586; A61M 2205/8206; A61M 2025/09133; A61M 25/09041; A61M 2025/09175; A61B 1/0052; A61B 2017/00318; A61B 2017/00867; A61B 2017/00778; A61B 17/00234; A61B 2017/00398; A61B 2017/00411; A61B 2017/0046; A61B 2017/291; A61B 2034/303; A61B 1/01
    See application file for complete search history.

(56) References Cited

U.S. PATENT DOCUMENTS

| | | |
|---|---|---|
| 5,178,159 A | 1/1993 | Christian |
| 5,357,979 A | 10/1994 | Imran |
| 5,403,297 A | 4/1995 | Imran |
| 2003/0199818 A1 | 10/2003 | Waldhauser et al. |
| 2005/0277988 A1 | 12/2005 | Whittaker et al. |
| 2010/0193568 A1* | 8/2010 | Scheib ............. A61B 17/07207 227/176.1 |
| 2012/0116388 A1* | 5/2012 | Houser ............ A61B 17/00234 606/1 |
| 2012/0197190 A1 | 8/2012 | Suon et al. |
| 2015/0112139 A1* | 4/2015 | Fujitani ............. A61B 1/00066 600/117 |

* cited by examiner

MEDICAL DEVICE COMPRISING A SMART HANDLE FOR IMPROVING HANDLING OF AN ELONGATED FUNCTIONAL SYSTEM

FIELD

The present invention pertains to the field of surgical and/or medical instruments. In particular, the invention relates to a smart handle for easily, securely and more accurately manipulating an elongated functional system as a guidewire, inside the body of a subject.

BACKGROUND

Catheters and endoscopes are essential materials in the medical field. Indeed, these materials enable to access to diseased sites that need to be checked and/or treated via a blood vessel. Due to their fragile and thin mechanical structures and due to the complexity of the vascular network, the placement of catheters and/or endoscopes into the body of a patient can be difficult and often requires guides or handles for helping practitioners to manipulate them.

Guidewires are suitable tools for navigation in the vascular system of an individual. However, until now, the handling of these guidewires remains rudimentary, and consists in manually manipulating the guidewire from a fixed point on it. This manual handling of the guidewire poses problems of precision and scalability of the control of the guidewire because of its length and of the accessibility of the areas to be reached. Furthermore, when used, the guidewire can store energy and release it in an uncontrolled manner that may presents a danger for the patient.

In the field of catheters, there are sophisticated catheter control systems that have been developed for improving their handling in interventional radiology whereas there is no sophisticated control system suitable for guidewires.

For instance, for catheter control systems, the U.S. Pat. No. 5,357,979 is known. It relates to a flexible elongated device comprising a flexible elongated member having proximal and distal extremities, a shape-memory element is disposed in the flexible elongate member and is capable of assuming martensitic and austenitic states and has first and second portions. A layer of conductive material is formed on at least one of said portions. The layer has a conductivity greater than that of the shape-memory element. Electrical current is supplied to the shape-memory element. The conductive layer serves to conduct current and shunts current flow around that portion of the shape-memory element having the layer of conductive material thereon. However, this invention does not provide its user with enough electrical security during use.

The U.S. Pat. No. 5,178,159 is also known for disclosing another guide wire assembly with first and second conductors which extend along the length thereof and a flexible cable. Such prior art document disclosed an apparatus that is rather inconvenient for driving a cable in a tortuous conduct path.

Eventually, the document EP0543539 disclosed also a steerable flexible elongate device comprising a flexible elongate member having proximal distal extremities and having a centrally disposed lumen extending into the distal extremity. The flexible elongate member of this document has at least three additional lumens spaced apart circumferentially about the centrally disposed lumen and extending into the distal extremity. A stiffener element is disposed in the centrally disposed lumen and has proximal and distal extremities. Additional flexible elongate elements having a negative coefficient of expansion are disposed in each of the three additional lumens and have proximal and distal extremities. The distal extremities of the stiffener element and the additional flexible elongate elements are secured to the distal extremity of the flexible elongate member. The proximal extremities of the stiffener element and the additional flexible elongate elements are also secured relative to the distal extremity of the flexible elongate member. This device is complex and not convenient for an easy use by a practitioner due to its size and the numerous different and separated composing elements.

Thus, there is still a need to provide optimized control systems such as handles, for guidewires. Especially, there is a need for providing electronical compact handles for guidewires to overcome the drawbacks as defined hereinabove.

SUMMARY

Thus, the present invention relates to a medical device comprising:
  an elongated functional system comprising a body part, said elongated functional system comprising at least one active area and optionally a sheath; said active area comprising at least one actuator connected to a first electrical interface comprising two circular conductive elements by two electrical conductors, said electrical conductors extending from the first active area to at least the proximal end of the body part; and
  a handle for manipulating the elongated functional system, comprising a handle body extending along a longitudinal axis comprising a chamber for receiving a power supply; and a power supply which is connected to a second electrical interface; at least one first external command, said first external command being arranged on the outer surface of the handle body, and the activation of said first external command allowing an electrical current to flow through at least two electrical connections between the first and second electrical interfaces; and
  a knob arranged on the distal part of the handle body, being rotatable around a rotation axis; and through which the proximal end of the elongated functional system is solidly anchored so that the rotation of the knob around the rotation axis leads to a rotation of the whole elongated functional system around the rotation axis,
wherein one of said electrical interface comprises at least two electrical connectors so that each electrical connector only connects with one of the at least two circular conductive elements of the other electrical interface, said electrical connectors comprising at their distal end a round tip for ensuring a permanent contact between the electrical connectors and the circular conductive elements during rotation. said second electrical interface comprises at least two electrical connectors so that each electrical connector only connects with one of the at least two circular conductive elements of the first electrical interface; said electrical connectors comprising at their distal end a round tip for ensuring a permanent contact between the electrical connectors and the circular conductive elements during rotation.

The round tip shape improves the contact surfaces and makes it smoother compared to other types of contact areas.

The electrical connectors are pressuring elastic means. They may have, in another preferred embodiment, the shape of a blade or a spring blade, or even a piston. In all cases, the tip remains preferably a round tip.

The expression "solidly anchored" refers to two elements attached to each other or physically linked to each other. It is mentioned that the elongated functional system is however removable and replaceable from the handle.

In a preferred embodiment, the elongated functional system comprises a second active area; said second active area comprising a second actuator connected to the first electrical interface by two other electrical conductors; and the handle for manipulating the elongated functional system, comprising a second external command, said second external command being arranged on the outer surface of the handle body, and the activation of said second external command allowing an electrical current to flow through two other electrical connections between the first and second electrical interfaces.

It is possible to have three electrical conductors, two for the electricity supply and one ground.

Preferably, the actuator is a shape memory alloy (SMA) wire, such configuration allows easier return to initial position.

Preferably, the elongated functional system is a guidewire.

In another embodiment, the first and second external commands are arranged on the surface of the handle body at different angular and radial positions with respect to the longitudinal axis of the handle body. This improves convenience for the practitioner.

Preferably, the two circular conductive elements are in coplanar arrangement, this embodiment, when combined with the use of a printed circuit board or electronic card, allows batch fabrication with a standardized process.

Alternatively, the two conductive elements may be in two different parallel planes. If the possibility of using multilayer assembly of conductive material is contemplated for the circular conductive elements, such a non-planar arrangement allows an easier production and process assembly of the device according to the invention.

In a preferred embodiment, the first electrical interface comprises more than two conductive elements, preferably comprises 4 conductive elements. This increases the number of electrical functions possibilities of the device according to the invention.

Preferably, the power supply is detachable.

In a preferred embodiment, the knob comprises a plurality of peaks or grooves on its outer surface.

Even more preferably, the knob comprises an indicator for giving visual information of a rotation, optionally with respect to another indicator arranged on the handle body.

Ideally, the handle is hermetic not to allow any liquid to enter the device according to the invention.

In another preferred embodiment, the elongated functional system has a mechanical connection to the handle, the elongated functional system being removable and replaceable by another one having a different function and/or length. This will allow changing the elongated functional system in case of malfunction also, improving lifetime of the device according to the invention.

More flexibility is offered to the practitioner.

In a preferred embodiment, the medical device according to the invention has two electrical interfaces that are located inside the handle and the mechanical connection is in between the elongated functional system and the handle.

In another preferred embodiment, the medical device according to the invention has one of the two electrical interfaces that is located inside the handle, the other electrical interfaces being located inside the knob, the mechanical connection is located in between the elongated functional system and the handle.

In another embodiment, the device according to the invention may further comprise a detaching means such as a trigger spring (160) disposed between the first and second electrical interfaces so as to disconnect said electrical interfaces from one to the other in case of emergency. In this case, once the trigger spring (160) is relaxed, its relaxation separates the two electrical interfaces. The separation takes place instantaneously and simultaneously for all circular conductive elements. The positioning, compression and calibration of the spring is known from the man skilled in the art. Different configurations can be used, the objective being to use a detaching means such as a spring able to separate the electrical interfaces.

In the present invention, the following terms have the following meanings:

"About" when placed before a figure, means plus or minus 10% of the figure.

"Actuator": can be any type of string, cable, wire, ribbon, tube or any set of those, capable of activating the body part to which it is fixed in order to trigger a function or to induce a bending of an area of the body part to which it is fixed. Actuators are materials and devices that are able to change their shape in response to changes in environmental conditions and perform mechanical work. An actuator may convey energy. Most of the time, an actuator transforms the received energy into another type of energy. In one embodiment, the actuator receives heat, and upon reception of the heat, it contracts. In one embodiment, the actuator is a shape memory alloy (SMA) wire.

"Active area" should be understood as a zone or a region of the system which is in relation with at least one actuator. In one embodiment, an active area is an area where an actuator is fixed. In one embodiment, the active area is an area capable of curvating when at least one actuator, fixed at least at the limits of the area, is activated.

"Catheter" is a tubular medical device for insertion into canals, vessels, passageways or body cavities for diagnostic or therapeutic purposes such as to permit injection/withdrawal of fluids, to keep passageways open, to inspect internal organs and tissues and to place medical tools into position for medical treatment within the body of an animal or of a human. In this invention, the term "catheter" encompasses any cannula or medical probe designed for insertion in a human or animal canal, vessel, passageway or body cavity.

"Wire" refers to a longitudinal means comprising a length sensibly higher than its thickness, its width or its diameter. In one embodiment the wire is a strand. In another embodiment, the wire is a very flexible rod. In one embodiment, the diameter of the wire ranges from 0.01 mm to 1 mm.

"to curvate" means to take the form of a curvature, to bend. Having a curvature or being curved is used in opposition to being straight. The term curvature means non-zero curvature. The curvature can be positive or negative.

"Handle" refers to a part of an object designed for being held.

"Flexible": refers to an object that may bend without breaking.

"Sterile": refers to any objet or part of object which is free of microbial germ or toxic product of microbial or fungal origin.

"Tubular medical guide": refers to any object under the form of a tube that is suitable for medical applications. According to one embodiment, the elongated functional system is a tubular medical guide, preferably is selected from a catheter, a guidewire or an endoscope.

BRIEF DESCRIPTION OF THE DRAWINGS

The detailed description will be better understood when read in conjunction with the drawings. For the purpose of illustrating, the handle 1 is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

DETAILED DESCRIPTION

Figure 1:
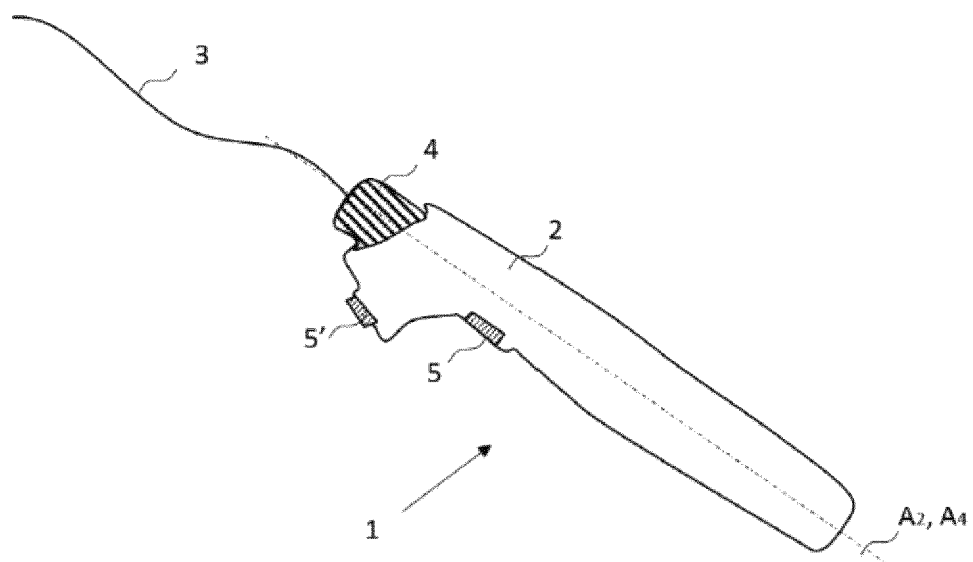
FIG. 1 and FIG. 2 are a side view of two versions of the handle 1 of the invention.

This invention relates to a medical device comprising a handle 1 for moving an elongated functional system 3 inside the body of a subject.

According to one embodiment, the handle 1 is for introducing, guiding, advancing, emplacing, rotating, activating, power supplying or/and holding an elongated functional system 3, such as for example, catheters or endoscopes or active guidewire, in veins or arteries. According to one embodiment, the handle 1, preferably the outer surface of the handle and the elongated system are sterile for limiting or avoiding the proliferation of pathogenic microorganisms.

According to one embodiment, the handle 1 comprises a handle body 2, at least one external command 5 and a knob 4.

According to one embodiment, the handle body 2 is adapted to human prehension so that it improves the comfort of hand position. According to one embodiment, the handle body 2 is adapted to the hand of an adult. According to one embodiment, the handle body 2 has ergonomics adapted to a left-handed person. According to one embodiment, the handle body 2 has ergonomics adapted to a right-handed person.

According to one embodiment, the handle body 2 extends to a longitudinal axis A2 from its proximal end to its distal end. According to one embodiment, the handle body 2 is cylindrical, parallelepiped, cone-shaped, ovaloid, pyramidal or multiform. According to one embodiment, the handle body 2 is under a form adapted to its grip by a practitioner. According to one embodiment, the handle body 2 is under a form particularly adapted to its grip by a practitioner wearing medical gloves; for example the handle body 2 comprises an anti-slip coating. According to one embodiment, the anti-slip coating includes the presence of indentations or a sandy zone.

According to one embodiment, the handle body 2 has a length lower than 16 cm so that it is adapted to a small hand. According to one embodiment, the handle body 2 has a length ranging from 16 cm to 20 cm so that it is adapted to a standard hand. According to one embodiment, the handle body 2 has a length higher than 20 cm so that it is adapted to a big hand.

According to one embodiment, the handle body 2 has a mean diameter, a section or a width ranging from 1 cm to 5 cm; preferably is about 1, 2, 3, 4 or 5 cm.

According to one embodiment, the handle body 2 has a constant section over its entire length. According to one embodiment, the handle body 2 has varied section over its entire length.

According to one embodiment, the handle body 2 has a weight ranging from 50 g to 500 g. According to one embodiment, the handle body 2 has a weight ranging from 50 g to 300 g adapted to a prolonged use of the handle.

According to one embodiment, the handle body 2 is made in metal so that allowing cleaning and resterilization. According to one embodiment, the handle body 2 is made in a renewable matter so that allowing recycling it and limiting the environmental impact after being used. According to one embodiment, the handle body 2 is made in a matter for being easily washed, sterilized and/or decontaminate. According to one embodiment, the handle body 2 is made in a matter that guarantees a complete seal of the inside of said handle body 2. According to one embodiment, the handle body 2 comprises or consists of polymer. According to one embodiment, the handle body 2 comprises or consists of polyurethane or fluorinated polymers. According to one embodiment, the handle body 2 comprises or consists of stainless steel.

According to one embodiment, the surface of the handle body 2 comprises a coating. According to one embodiment, the surface of the handle body 2 comprises an anti-slip coating for increasing the grip of the handle body by practitioner during its use, especially when the surface of the handle body 2 becomes wet. According to one embodiment, the surface of the handle body 2 comprises a coating for preserving sealing of the inside of the handle body 2.

According to one embodiment, the coating is on the whole surface of the handle body 2. According to one embodiment, the coating is on a part of the surface of the handle body 2. According to one embodiment, the whole handle body 2 is obtained by a one-step molding, in order to improve sealing of the handle body 2. According to one embodiment, at least two parts of the handle body 2 are obtained by molding and then assembling, in order to facilitate the insertion of additional functional elements inside said handle body. According to one embodiment, the handle body 2 is obtained by 3D printing. Advantageously, manufacturing the handle body by 3D printing allows easy modulating the dimensions and/or the functional characteristics of said handle body.

According to one embodiment, the handle body 2 comprises a chamber 21 adapted to the insertion of additional functional elements. According to one embodiment, the shape of the chamber 21 is the same as the handle body 2, as defined above. According to one embodiment, the chamber is adapted for receiving a power supply 211. According to one embodiment, the chamber 21 and the power supply 211 have complementary shapes in order to optimize the insertion and/or the removing of the power supply inside the handle body. According to one embodiment, the power supply 211 is a battery or an accumulator, preferably selected from AA and AAA batteries. According to one embodiment, the power supply 211 is rechargeable in order to limit the environment effect. According to one embodiment, the power supply 211 is a battery with one or two lithium ion cells.

According to one embodiment, the handle body 2 and/or the chamber 21 further comprises electrical connectors 212. According to one embodiment, the power supply 211 directly connects to the electrical connectors 212 inside the handle body 2. According to one embodiment, the power supply 211 directly connects to an electrical interface EI2 comprising electrical connectors 212, said electrical interface EI2 being inside the handle body 2. According to one embodiment, the electrical interface EI2 is circular. The connection from the power supply 211 can also be with EI1.

According to one embodiment, the chamber 21 comprises an opening 213. According to one embodiment, the opening 213 is at the proximal end of the handle body 2. According to one embodiment, the opening 213 is at the distal end of the handle body 2. According to one embodiment, the opening 213 is on one side of the handle body 2.

According to one embodiment, the handle 1 comprises at least one external command 5 for activating an elongated functional system 3, preferably for activating at least one active area 31 of the elongated functional system 3, more preferably for activating at least one actuator 32 such as for example a shape memory wire. According to one embodiment, the handle 1 comprises two external commands 5, 5' for activating an elongated functional system 3. According to one embodiment, each external command 5 or 5' on the handle 1 allows activating a different active area of the elongated functional system 3.

According to one embodiment, the external command 5 is flush with the surface of the handle body 2. According to one embodiment, the top of the external command 5 is outside the surface of the handle body 2.

According to one embodiment, at least one external command 5 is ergonomic, that-is-to say is adapted to the finger of the practitioner. For example, the ergonomic external command 5 is circular or cylindrical, or has a curved shape. According to one embodiment, at least one external command 5 is adapted to thumb. According to one embodiment, at least one external command 5 is adapted to index finger. According to one embodiment, at least one external command 5 is adapted to middle finger. According to one embodiment, at least one external command 5 is adapted to ring finger. According to one embodiment, at least one external command 5 is adapted to baby finger. According to one embodiment, the external command 5 may be parallelepiped or cubic.

According to one embodiment, the external command 5 is a button or a pushbutton. According to one embodiment, the external command 5 comprises a spring leading to a springing force when pressed, and allows giving more accurate information to the practitioner regarding the activation of the shape memory alloy wire. According to one embodiment, the external command 5 comprises a touch zone so that the more the external command 5 is pressed, the stronger is the activation.

According to one embodiment, the external command 5 is an illuminated button or comprises or is linked to an operating light. According to one embodiment, the light color of the illumination indicates the actionized portion of the elongated functional system 3.

According to one embodiment, the surface of the external command 5 comprises small dots in extra thickness or grooves, in order to sensory modulate the action of external command 5. According to one embodiment, the mean diameter or the length of the external command 5 ranges from 5 mm to 20 mm in order to be adapted to a human finger.

According to one embodiment, two external commands 5 are arranged on the outer surface of handle body 2. According to one embodiment, the handle body 2 comprises a first external command 5 and a second external command 5' arranged on the surface of the handle body 2 at different longitudinal positions with respect to the axis of the handle body 2. According to one embodiment, the first external command 5 and the second external command 5' are arranged on the surface of the handle body 2 at different angular and radial positions with respect to the axis of the handle body 2. According to one embodiment, when the practitioner holds the handle 1, a first external command 5 is arranged for the thumb and a second external command 5' is arranged for the index finger. According to one embodiment, when the practitioner holds the handle 1, a first external command 5 is arranged for the thumb and a second external command 5' is arranged for the middle finger. According to one embodiment, when the practitioner holds the handle 1, a first external command 5 is arranged for the index finger and a second external command 5' is arranged for the middle finger. According to one embodiment, when the practitioner holds the handle 1, a first external command 5 is arranged for the middle finger and a second external command 5' is arranged for the ring finger.

According to one embodiment, the external command 5 is in metal or polymer. According to one embodiment, the external command 5 is hermetic. According to one embodiment, the external command 5 comprises a seal.

According to one embodiment, the external command 5 is rest contact button. According to one embodiment, the external command 5 is a closer button. According to one embodiment, the activation of the first external command 5 and/or the second external command 5' allows an electrical current to flow through to an electrical interface EI. According to one embodiment, the activation of the first external command 5 and/or the second external command 5' generate(s) an electrical signal which will be received by an electrical interface EI, and allow(s) controlling the quantity of current send to the elongated functional guide 3.

According to one embodiment, the first electrical interface EI1 is intended to be in contact with at least one electrical conductor 312, preferably with at least two electrical conductors 312, of the elongated functional system 3. According to one embodiment, the first electrical interface EI1 is intended to be in contact with all the electrical conductors 312 connected to the actuators of the elongated functional system 3. According to one embodiment, the first electrical interface EI1 comprises at least one conductive element EC, preferably circular, such as for example a circular electrical circuit, more preferably the first electrical interface EI1 comprises at least two co-axial circular conductive elements. According to one embodiment, the first electrical interface EI1 comprises as many circular electrical conductive elements (EC) as electrical conductors 312 connected to the actuators of the elongated functional system 3. In a particular case, the two grounds of the co-axial circular conductive elements are connected to the same electrical circuit. In another preferred embodiment, the at least two co-axial circular conductive elements of the first electrical interface EI1 are also coplanar as in FIG. 7. This ensures easier assembly process or production steps.

According to one embodiment, in case the elongated functional system 3 is a removable one, the mechanical connection between the elongated functional system 3 and the handle 2 can independently be located either before, after or in between the electrical interfaces (EI1 and EI2) depending on the handle design.

According to one embodiment, the activation of the first external command 5 allows a first electrical current to flow to a first electrical interface EI1 by a conductive element EC1. According to one embodiment, the first electrical interface EI1 is intended to be in contact with at least one electrical conductor 312 of the elongated functional system 3, preferably with at least two electrical conductors 312 of the elongated functional system 3. Said electrical conductors 312 being in contact with either the conductive element EC1 or EC2 on the electrical interface EI1.

According to one embodiment, the activation of the second external command 5' allows a second electrical current to flow to a second conductive element EC. According to one embodiment, the second conductive element EC is intended to be in contact with at least one electrical conductor of the elongated functional system 3, preferably with at least two electrical conductors 312 of the elongated functional system 3.

According to one embodiment, the first conductive element EC1 and the second conductive element EC2 are arranged on the same electronic card, preferably a circular electronic card. According to one embodiment, the electronic card has a shape adapted to its insertion in the chamber 21 and/or in the handle body 2. According to one embodiment, the first electrical interface EI1 comprises at least two conductive elements EC1 and EC2. According to one embodiment, the first electrical interface EI1 comprises or consist of the superposition of at least two electronic cards.

The electrical connection between the first electrical interface EI1 is connected to the proximal part of the knob 4 and includes two co-axial circular conductive elements EC1 and EC2 that rotate around their common axis $A_2$; It also includes a second electrical interface EI2 comprising two electrical connectors (212a and 212b) arranged on said second electrical interface EI2 so that each electrical connector 212 only connects with one of the two co-axial circular conductive elements EC1 and EC2. It is to be noted that the two electrical connectors 212a and 212b of EI2 and the two circular conductive elements EC1 and EC2 of the first electrical interface EI1 have interchangeable positions between the two interfaces.

According to one embodiment, the first electrical interface, the second electrical interface are located inside the handle body 2, preferably inside the chamber 21. According to one embodiment, the first and second circular conductive elements are in co-axial and coplanar arrangement.

According to one embodiment, the external command 5" is arranged on the surface of the handle body 2. According to one embodiment, the external command 5" allows the flow of a third electrical current. According to one embodiment, the third electrical current goes through the first and the second electrical interface. According to one embodiment, the third electrical current goes through third pair of electrical connectors in contact with a third pair of circular electrical elements located on EI1 and EI2. According to one embodiment, when the practitioner holds the handle 1, a third external command 5" is arranged for the thumb. According to one embodiment, when the practitioner holds the handle 1, a third external command 5" is arranged for the index finger. According to one embodiment, when the practitioner holds the handle 1, a third external command 5" is arranged for the middle finger.

According to one embodiment, the knob 4 is arranged on the distal part of the handle body.

According to one embodiment, the knob 4 moves around a rotation axis A4 of the handle body 2. According to one embodiment, the longitudinal axis A2 of the handle body 2 and the rotation axis A4 of the knob 4 are the same. According to one embodiment, the longitudinal axis A2 of the handle body 2 and the rotation axis A4 of the knob 4 are different, preferably the longitudinal axis A2 of the handle body 2 and the rotation axis A4 of the knob 4 are offset from each other.

According to one embodiment, the knob 4 is in the axis of the handle body 2. According to one embodiment, the knob 4 is perpendicular to the axis of the handle body 2. According to one embodiment, the knob 4 is adapted to the shape of the handle body 2. According to one embodiment, the knob 4 is cylindrical, spherical, cubic, parallelepiped, ovaloid or pyramidal, preferably the knob 4 is cylindrical. According to one embodiment, the knob 4 comprises an opening for receiving at least one elongated functional system 3. According to one embodiment, the elongated functional system 3 crosses the knob 4, preferably along the rotation axis A4 of said knob.

According to one embodiment, the knob 4 comprises a size superior to the section of the handle body 2. According to one embodiment, the size of the knob 4 such as for example, its mean diameter, ranges from 1 cm to 3 cm. According to one embodiment, the size of the knob 4 such as for example, its mean diameter, is higher than 2 cm for getting a finer setting. According to one embodiment, the size of the knob 4 such as for example, its mean diameter, ranges from 1 to 2 cm for limiting clutter. According to one embodiment, the diameter is variable and can be adjusted to the targeted use.

According to one embodiment, the knob 4 is made in a matter for being easily washed, sterilized and/or decontaminate. According to one embodiment, the knob 4 is made in a matter that guarantees a complete seal of the inside of said knob. According to one embodiment, the knob 4 comprises or consists of polymer. According to one embodiment, the knob 4 comprises or consists of polyurethane or fluorinated polymers. According to one embodiment, the knob 4 comprises or consists of stainless steel.

According to one embodiment, the surface of the knob 4 comprises a plurality of peaks or grooves on its outer surface, for improving the human prehension. According to one embodiment, the grooves of the knob are parallel or perpendicular to the axis of the handle body 2. According to one embodiment, the knob 4 comprises a position indicator for locating the turning portion engaged by said knob with respect to an initial position of said knob 4.

According to one embodiment, the position indicator is a peak or a specific groove. According to one embodiment, before being used, the knob 4 is in an initial position where the position indicator of the knob faces to a visual reference arranged on the handle body 2. According to one embodiment, the position indicator of the knob 4 is for improving the control and/or the rotation evolution of said knob. According to one embodiment, the position indicator of the knob 4 comprises a digital display for counting the number of rotations of the knob around the rotation axis A4. According to one embodiment, the position indicator of the knob 4 comprises a digital display for indicating the angle traveled by said knob with respect to its initial position.

According to one embodiment, the knob 4 is intended to generate a radial movement of the elongated functional system 3, with respect to the axis of the handle body 2. According to one embodiment, the knob 4 allows a free return to the initial position. According to one embodiment, the knob 4 has a position for blocking its rotation. According to one embodiment, the knob 4 comprises a friction system limiting the free rotation of said knob.

According to one embodiment, the knob 4 is hermetic. According to one embodiment, the knob 4 comprises a seal.

According to one embodiment, the handle 1 further comprises an illuminating assembly and/or a video system. According to one embodiment, the illuminating assembly and/or the video system is (are) located inside the handle body 2. According to one embodiment, the illuminating assembly and/or the video system is (are) arranged on the outer surface of the handle 1. According to one embodiment, the illuminating assembly and/or the video system is (are) arranged on the proximal end of the handle. According to one embodiment, the illuminating assembly and/or the video system is (are) arranged on the distal end of the handle 1. According to one embodiment, the video system is a camera. According to one embodiment, the handle 1 is connected to a screen for following the guide's progress inside the human body.

According to one embodiment, the handle 1 further comprises a chamber for a therapeutically solution or for physiological serum. According to one embodiment, the handle 1 further comprises a suction system. According to one embodiment, the handle 1 is connected to an external medical device such as a medical pump or a coil delivery system for example.

According to one embodiment, the handle 1 further comprises means for inserting a powers supply inside or connecting power supply on said handle.

Figure 2:
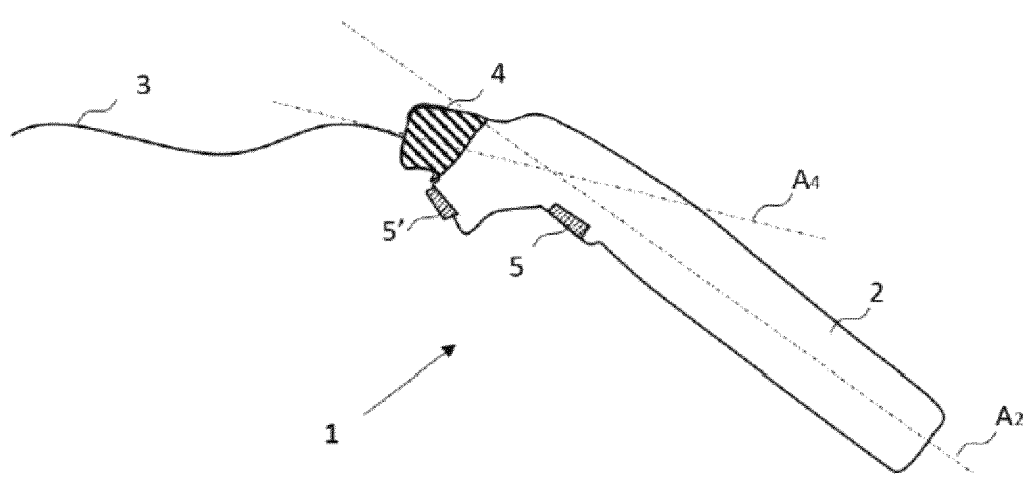

FIG. 1 and FIG. 2 are a side view of two versions of the handle 1 of the invention. The handle 1 comprises a handle body 2 extending from a first axis A2 with two external commands 5 and 5' allowing activating or not the elongated functional system 3. The knob 4 directly connects to the elongated functional system 3 so that any action on the knob 4 implies a move of the elongated functional system 3 around a rotation axis A4. In FIG. 1, the rotation axis A4 of the knob 4 and the axis A2 of the handle body 2 are the same. In FIG. 2, the rotation axis A4 of the knob 4 and the axis A2 of the handle body 2 are offset each other.

Figure 3:
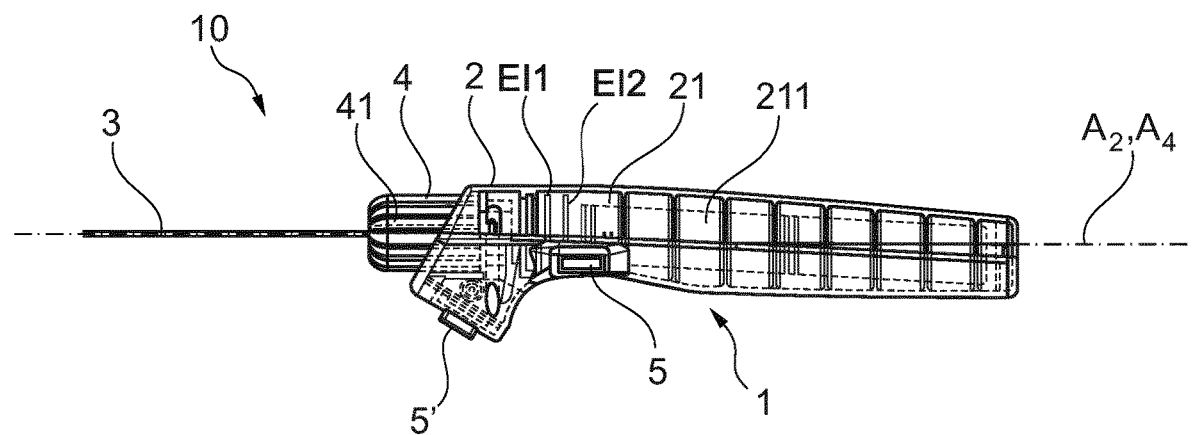
FIG. 3 is a perspective side view of the handle 1 of the invention as defined in FIG. 1.

FIG. 3 is a perspective side view of the handle 1 of the invention as defined in FIG. 1. FIG. 3 shows the elements of the handle body 2 that comprises batteries 211 located in a chamber 21 so that batteries are directly connected to an electrical interface EI2. Batteries 211 are located inside the chamber 21.

Figure 4:
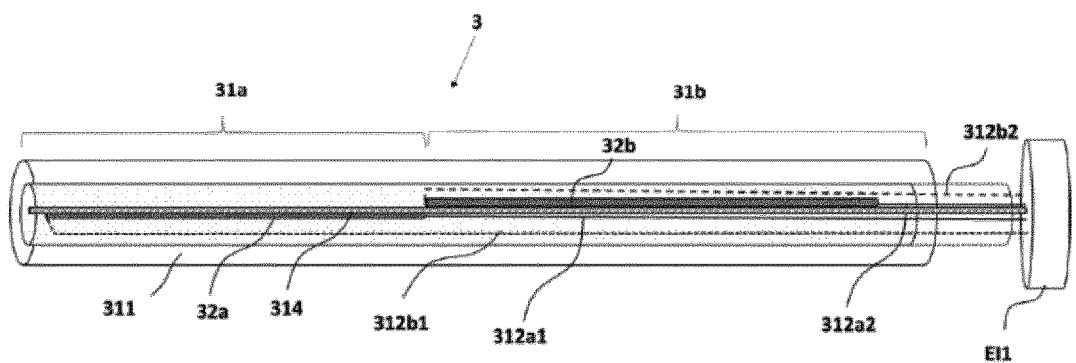
FIG. 4 is a schema of the elongated functional system 3 including two active areas (31a and 31b) arranged on a body part 314 and surrounded by a sheath 311.

FIG. 4 is a schema of the elongated functional system 3 including two active areas (31a and 31b) arranged on a body part 314 and surrounded by a sheath 311. Each active area 31 comprises an actuator 32 being connected to two electrical connectors 312 (an incoming electrical wire (312a) and an outcoming electric wire (312b)) so as to form an electrical circuit with the electrical interface EI1. When the electrical current circulates in the electrical circuit, the actuator 32 acts as a resistance and its heating leads to the contraction of the actuator 32 and the formation of a curvature. The radius of curvature depends on the intensity of current sent to the actuator 32 by the power supply 211 and the physical properties of the actuator 32.

Typically, EI1 and EI2 are connection cards with an electrical functional system connected to a power supply that can be, in this invention, optionally detachable.

Figure 5:
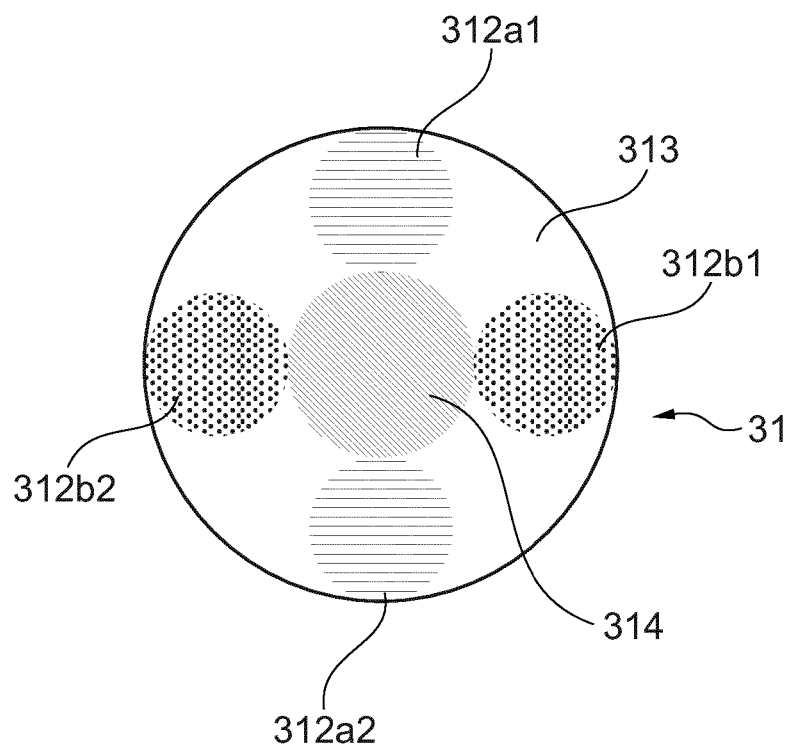
FIG. 5 is cutting view of a body part (314) comprising a core around which are wound copper wires (312a1, 312a2, 312b1, 312b2).

FIG. 5 is cutting view of a body part (314) comprising a core around which are wound copper wires (312a1, 312a2, 312b1, 312b2).

Figure 6:
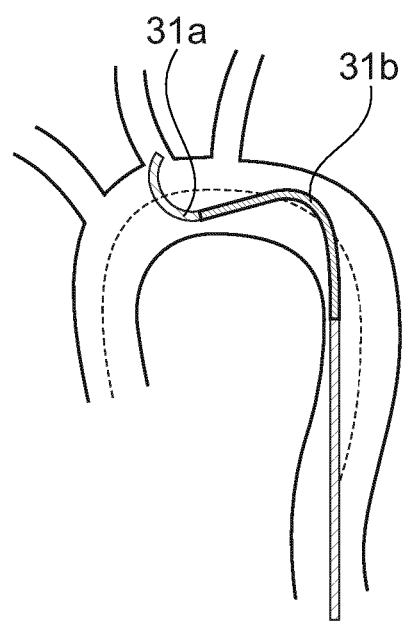
FIG. 6 is a scheme showing the use of the elongated functional system 3 as defined in FIG. 3, inside the aortic arch.

FIG. 6 is a scheme showing the use of the elongated functional system 3 as defined in FIG. 3, inside the aortic arch.

Figure 7:
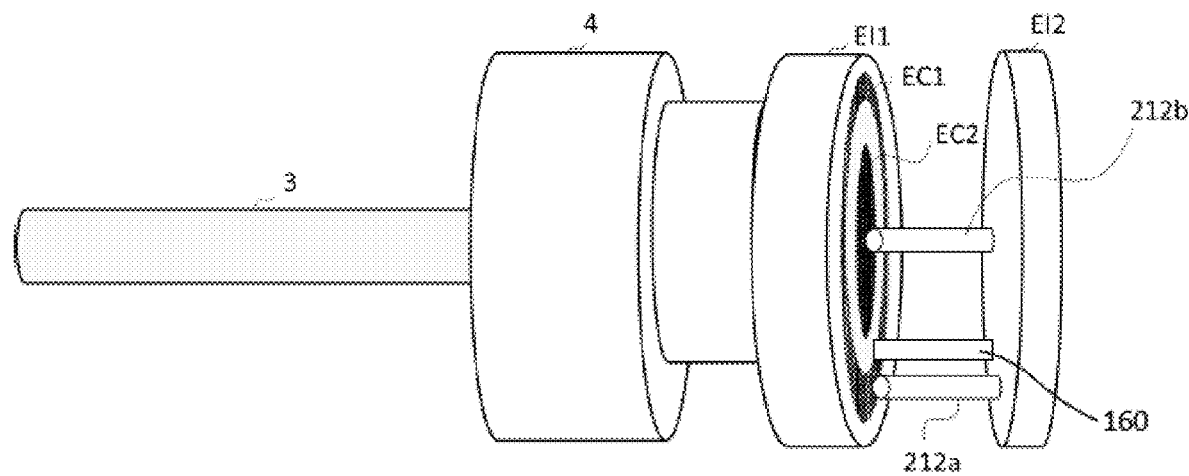
FIG. 7 is a scheme showing the electrical connection between the first electrical interface and the second electrical interface including two electrical connectors.

FIG. 7 is a scheme showing the electrical connection between the first electrical interface EI1 being connected to the proximal part of the knob 4 and including two co-axial circular conductive elements EC1 and EC2 that rotate around their common axis $A_2$; and a second electrical interface EI2 including two electrical connectors (212a and 212b) arranged on said second electrical interface EI2 so that each electrical connector 212 only connects with one of the two co-axial circular conductive elements EC1 and EC2.

Uses

The invention also relates to the use of the handle 1 as defined above, preferably in medical applications.

According to one embodiment, the handle 1 as defined above is for use in interventional radiology or cardiology. According to one embodiment, the handle 1 as defined above is for use in surgery. According to one embodiment, the handle 1 as defined above is for use in cardiovascular surgery. According to one embodiment, the handle 1 as defined above is for use in ophthalmic surgery.

According to one embodiment, the handle 1 as defined above, is for use in diagnostic endoscopy. According to one embodiment, the handle 1 as defined above is for body navigation by a catheter. According to one embodiment, the handle 1 as defined above, is for a delivering therapeutic solution or a physiological serum to a targeted site in the body of a subject.

While various embodiments have been described and illustrated, the detailed description is not to be construed as being limited hereto. Various modifications can be made to the embodiments by those skilled in the art without departing from the scope of the disclosure as defined by the claims.

The invention claimed is:

1. A medical device comprising:
   an elongated functional system comprising a body part, said elongated functional system comprising at least a first active area and optionally a sheath; said at least a first active area comprising at least one actuator connected to a first electrical interface comprising two co-axial circular conductive elements by two electrical conductors, said electrical conductors extending from the at least a first active area to at least a proximal end of the body part; and
   a handle for manipulating the elongated functional system, comprising:
   a handle body extending along a longitudinal axis comprising a chamber for receiving a power supply; and a power supply which is connected to a second electrical interface;
   at least one first external command, said first external command being arranged on the outer surface of the handle body, and the activation of said first external command allowing electrical current to flow through at least two electrical connections between the first and second electrical interfaces; and
   a knob arranged on the distal part of the handle body, being rotatable around a rotation axis; and through which the at least a proximal end of the elongated functional system is solidly anchored so that the rotation of the knob around the rotation axis leads to a rotation of the whole elongated functional system around the rotation axis, wherein one of said electrical interface comprises at least two electrical connectors so that each electrical connector only connects with one of the at least two circular conductive elements of the other electrical interface; said electrical connectors comprising at their distal end a round tip for ensuring a permanent contact between the electrical connectors and the circular conductive elements during rotation;

wherein the at least two conductive elements are in coplanar arrangement, and on a printed circuit board which is perpendicular to the longitudinal axis of the handle body.

2. The medical device according to claim 1, wherein:
the elongated functional system comprises a second active area; said second active area comprising a second actuator connected to the first electrical interface by two other electrical conductors; and the handle for manipulating the elongated functional system, comprising a second external command, said second external command being arranged on the outer surface of the handle body, and the activation of said second external command allowing an electrical current to flow through two other electrical connections between the first and second electrical interfaces.

3. The medical device according to claim 1, wherein the actuator is a shape memory alloy (SMA) wire.

4. The medical device according to claim 1, wherein the elongated functional system is a guidewire.

5. The medical device according to claim 1, wherein the two conductive elements are in two different parallel planes.

6. The medical device according to claim 1, wherein the first electrical interface comprises more than two conductive elements.

7. The medical device according to claim 1, wherein the power supply is detachable.

8. The medical device according to claim 1, wherein the knob comprises a plurality of peaks or grooves on its outer surface.

9. The medical device according to claim 1, wherein the knob comprises an indicator for giving visual information of a rotation, optionally with respect to another indicator arranged on the handle body.

10. The medical device according to claim 1, wherein the elongated functional system has a mechanical connection to the handle, said functional system being removable and replaceable.

11. The medical device according to claim 10, wherein the two electrical interfaces are located inside the handle and the mechanical connection is in between the elongated functional system and the handle.

12. The medical device according to claim 10, wherein one of the two electrical interfaces is located inside the handle, the other electrical interfaces being located inside the knob, the mechanical connection is located in between the elongated functional system and the handle.

13. The medical device according to claim 1, further comprising a trigger spring disposed between the first and second electrical interfaces so as to disconnect said electrical interfaces in case of emergency.

* * * * *